US009254365B2

(12) United States Patent
Thorley et al.

(10) Patent No.: US 9,254,365 B2
(45) Date of Patent: Feb. 9, 2016

(54) CLINICAL SYRINGE WITH REPLACEABLE RETRACTABLE NEEDLE

(75) Inventors: Craig Stephen Thorley, Largs (AU); Joseph Hermes Kaal, Raworth (AU); Ian Johnson, Pennant Hills (AU); Andrew Reade, Castle Hill (AU); Eric Siu, Strathfield (AU); Richard Sokolov, Earlwood (AU); Christopher Dunn, Spring Farm (AU)

(73) Assignee: UNITRACT SYRINGE PTY LTD, Sydney (AU)

( * ) Notice: Subject to any disclaimer, the term of this patent is extended or adjusted under 35 U.S.C. 154(b) by 678 days.

(21) Appl. No.: 13/508,690

(22) PCT Filed: Nov. 11, 2010

(86) PCT No.: PCT/AU2010/001504
§ 371 (c)(1),
(2), (4) Date: Nov. 12, 2012

(87) PCT Pub. No.: WO2011/057334
PCT Pub. Date: May 19, 2011

(65) Prior Publication Data
US 2013/0060202 A1 Mar. 7, 2013

Related U.S. Application Data

(60) Provisional application No. 61/260,253, filed on Nov. 11, 2009.

(51) Int. Cl.
*A61M 5/32* (2006.01)
(52) U.S. Cl.
CPC ............ *A61M 5/3234* (2013.01); *A61M 5/3221* (2013.01); *A61M 2005/323* (2013.01); *Y10T 29/49826* (2015.01)

(58) Field of Classification Search
CPC ..................... A61M 2005/323; A61M 5/3234; A61M 5/3221
USPC .......................................... 604/110
See application file for complete search history.

(56) References Cited

U.S. PATENT DOCUMENTS 4,950,241 A 8/1990 Ranford
5,019,045 A * 5/1991 Lee ............................... 604/110
(Continued)

FOREIGN PATENT DOCUMENTS

JP 2003-205035 A 7/2003
WO 2004/052432 A 6/2004
(Continued)

OTHER PUBLICATIONS

Australian Patent Office, International Search Report in International Patent Application No. PCT/AU2010/00154 (Feb. 10, 2011).

*Primary Examiner* — Theodore Stigell
*Assistant Examiner* — Benjamin Koo
(74) *Attorney, Agent, or Firm* — Leydig Voit & Mayer, Ltd.

(57) ABSTRACT

A replaceable needle assembly is provided for a retractable syringe comprising a barrel and a plunger, whereby the retractable needle can be replaced by a user without affecting the retraction mechanism. A mounting member is removably mountable to the barrel by way of a screw-thread connection and a needle mount is removably coupled to the mounting member. A needle is mounted to the needle mount. The barrel comprises a needle mount retainer that comprises a plurality of fingers that engage the retractable needle mount to prevent inadvertent retraction. The plunger comprises a collapsible seal which maximizes the efficiency of fluid delivery prior to the plunger engaging the retractable needle mount for retraction. An initially compressed spring decompresses to drive retraction of the plunger and the engaged needle mount. A lock formed between the plunger and barrel prevents further use of the plunger after retraction.

32 Claims, 11 Drawing Sheets

(56) References Cited

U.S. PATENT DOCUMENTS

| | | | |
|---|---|---|---|
| 5,112,316 A * | 5/1992 | Venturini | 604/195 |
| 5,308,322 A * | 5/1994 | Tennican et al. | 604/83 |
| 5,584,817 A * | 12/1996 | van den Haak | 604/195 |
| 2002/0169421 A1 | 11/2002 | McWethy et al. | |
| 2006/0253074 A1 | 11/2006 | Thayer | |
| 2008/0208119 A1* | 8/2008 | Walton et al. | 604/110 |
| 2009/0221962 A1* | 9/2009 | Kaal et al. | 604/110 |
| 2011/0264040 A1* | 10/2011 | Li | 604/110 |

FOREIGN PATENT DOCUMENTS

| | | |
|---|---|---|
| WO | 2004/105842 A1 | 12/2004 |
| WO | 2005/072801 A1 | 8/2005 |
| WO | 2006/105583 A1 | 10/2006 |
| WO | 2006/108243 A1 | 10/2006 |
| WO | 2009/003234 A1 | 1/2009 |

\* cited by examiner

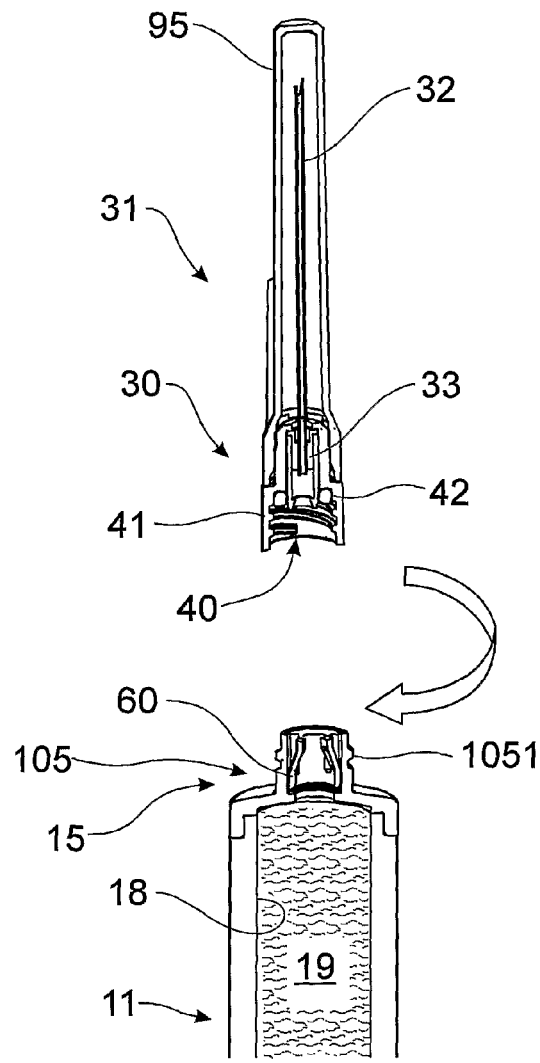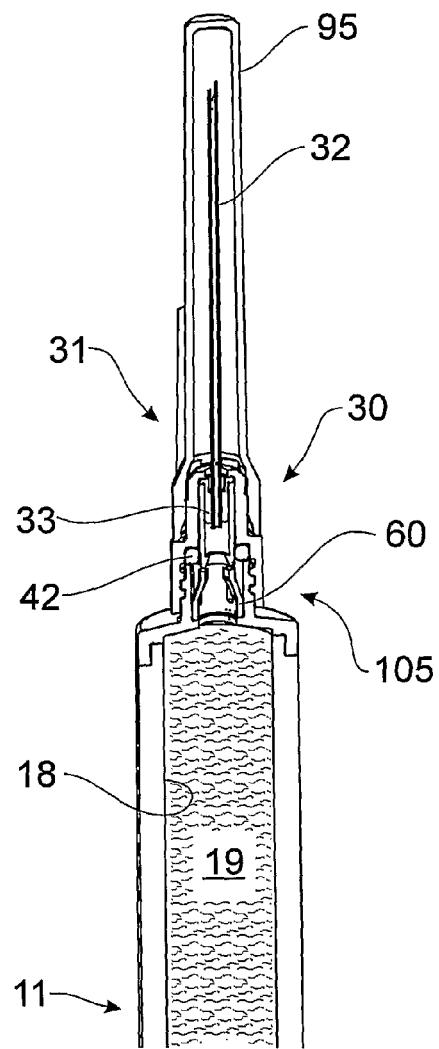
FIG. 5A                    FIG. 5B

CLINICAL SYRINGE WITH REPLACEABLE RETRACTABLE NEEDLE

CROSS-REFERENCE TO RELATED APPLICATIONS

This patent application is the U.S. national stage of International Patent Application No. PCT/AU2010/001504, filed Nov. 11, 2010, which claims the benefit of U.S. Provisional Patent Application No. 61/260,253, filed Nov. 11, 2009, the disclosures of which are herein incorporated by reference.

FIELD

THIS INVENTION relates to syringes. More particularly, this invention relates to a retractable syringe that includes a replaceable, retractable needle and a plunger capable of engaging the replaceable, retractable needle to facilitate retraction of the needle.

BACKGROUND

The practice of sharing syringes without adequate sterilization between successive users is a major contributor to the transfer of Human Immunodeficiency Virus (HIV) and Hepatitis C with subsequent severe repercussions for the sufferer and at a high cost to society for supporting and providing medical attention to sufferers. Further problems arise for health professionals administering medicines to infected individuals, where accidental needle stick injury by a used syringe can lead to infection.

In response to this problem, syringes have been developed which provide a needle sheathing mechanism and/or a needle retraction mechanism to prevent re-use and/or needle stick injury.

However, many such syringes have fixed needles or highly specialized needle assemblies that are not amenable to replacing needles which have been bent or burred or for allowing a user to select alternative needle sizes for filling and injection.

SUMMARY

The invention is therefore, at least in part, broadly directed to a replaceable needle assembly for a retractable syringe, whereby a retractable needle can be replaced by a user without affecting the retraction mechanism.

The invention is also broadly directed to a barrel suitable for mounting the replaceable needle assembly.

The invention further provides an improved plunger comprising a plunger seal that improves the efficiency of fluid delivery from a retractable syringe.

In a first aspect, the invention provides a replaceable needle assembly for a retractable syringe comprising a plunger and a barrel, said replaceable needle assembly comprising: a mounting member removably mountable to the barrel; a retractable needle mount removably mounted to the mounting member and engageable by said plunger; and a needle mounted to the needle mount.

In one embodiment the mounting member comprises a female member which receives a male member of said barrel.

Preferably, the mounting member comprises a screw-thread which receives a complementary screw thread of said barrel.

In a second aspect, the invention provides a barrel for a retractable syringe to which is removably mountable a replaceable needle assembly.

In one embodiment, said barrel comprises a male member receivable by a female member of said replaceable needle assembly.

Preferably, said barrel comprises a screw thread receivable by a complementary screw thread of the replaceable needle assembly.

In one embodiment, the barrel further comprises a needle mount retainer.

Preferably, the releasing member comprises fingers that retain said needle mount until retraction. In one particular embodiment, said fingers are movable radially outwardly to release said needle mount for retraction.

In one embodiment, the barrel further comprises a seal.

In one embodiment, the barrel further comprises a releasing member.

In a third aspect, the invention provides a plunger for a retractable syringe, said plunger comprising: a biasing means; a plunger inner; a plunger outer; and a collapsible seal mounted to the plunger inner; wherein the plunger inner and plunger outer co-operate to maintain said biasing means in an initially energized state prior to retraction.

Preferably, said plunger inner comprises a means for engaging a retractable needle mount of said replaceable needle assembly. More preferably, a needle is mounted to the retractable needle mount.

In a particular embodiment, said means for engaging the retractable needle mount comprises one or more barbed arms.

In a preferred embodiment, the plunger inner further comprises a trigger which initially engages said plunger outer to retain said biasing means in an initially energized state prior to retraction. Preferably, disengagement of said trigger from said plunger outer facilitates release of energy from said biasing means which facilitates retraction of said needle mount when coupled to said plunger inner.

Suitably, said biasing member is any device which can store energy in a releasable form, such as a spring, elastic or the like.

Preferably, said biasing means is a spring.

In one embodiment, the collapsible seal comprises an internal hollow chamber.

In a fourth aspect, the invention provides a retractable syringe kit comprising the barrel of the second aspect and the plunger of the third aspect in combination; and a plurality of replaceable needle assemblies according to the first aspect.

In one embodiment of the retractable syringe kit, the plurality of replaceable needle assemblies respectively comprise a 0.5 inch needle, a 1.0 inch needle and a 1.5 inch needle.

In a fifth aspect, the invention provides a retractable syringe comprising: the replaceable needle assembly of the first aspect removably mounted to the barrel of the second aspect; and/or the plunger of the third aspect.

In one embodiment, the retractable syringe further comprises a lock formed between said plunger outer and said barrel which prevents or hinders removal of the plunger outer from the barrel after retraction of the retractable needle mount.

In a sixth aspect, the invention provides a method of operating a retractable syringe including the step of removably mounting a replaceable needle assembly to a barrel of a retractable syringe after filling the barrel with fluid contents for subsequent delivery.

In one embodiment, the method includes the step of screw-threadedly mounting the replaceable needle assembly to the barrel.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to the following drawings wherein:

FIG. 5A is a sectional view of an embodiment of a barrel after filling with fluid contents and after removal of a replaceable needle assembly; and FIG. 5B is a sectional view showing the same embodiment where the replaceable needle assembly has been replaced by another replaceable needle assembly mounted to the barrel mounting member;

DETAILED DESCRIPTION

Figure 1:
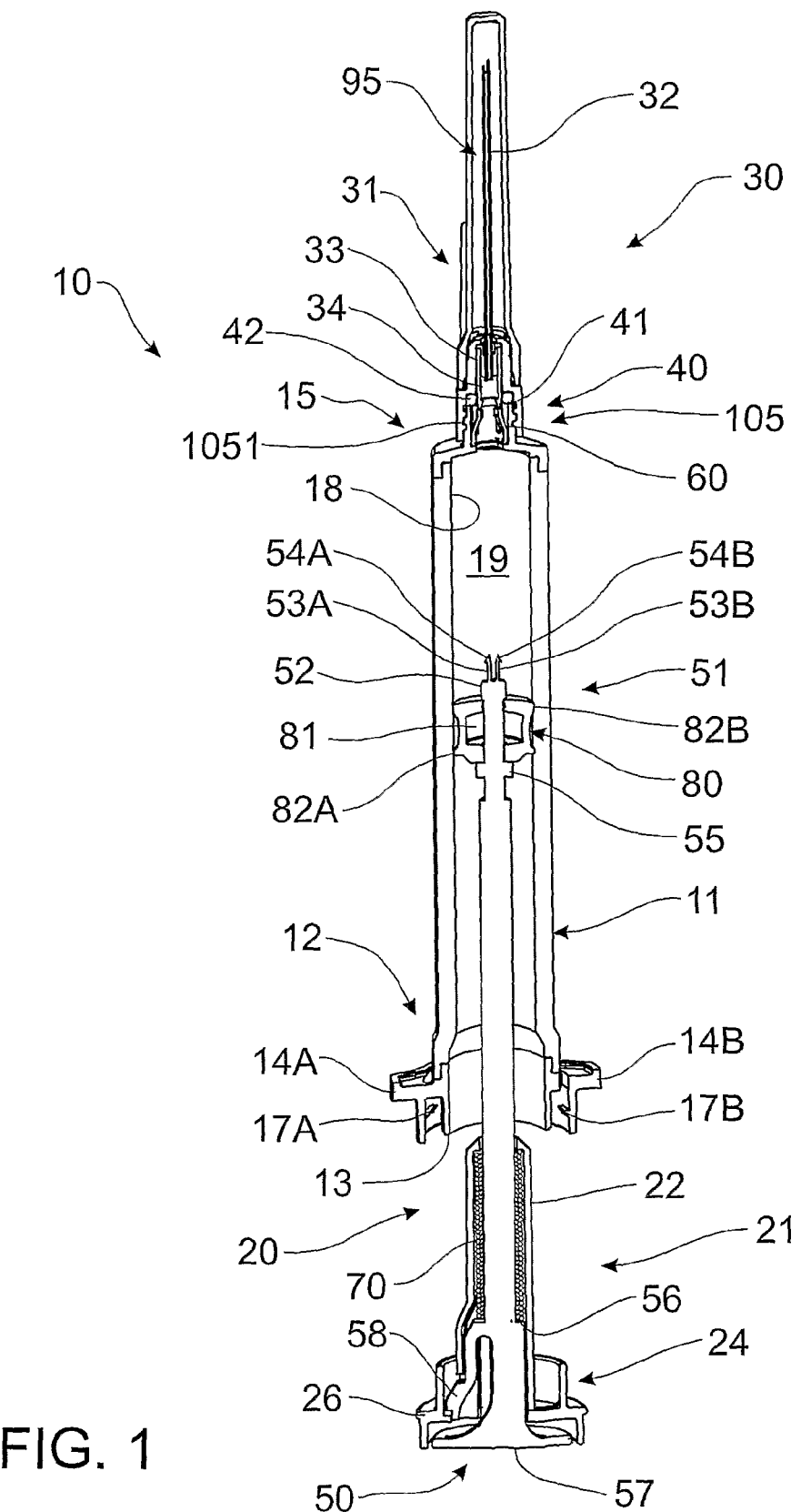
FIG. 1 is a sectional view of an embodiment of a retractable syringe.

Referring to FIG. 1, an embodiment of syringe 10 comprises barrel 11 and plunger 20 having plunger inner 50 and plunger outer 21. Plunger seal 80 is mounted to plunger inner 50. Plunger 20 is slidably, axially moveable within barrel 11 with plunger seal 80 forming a fluid-tight seal against inside wall 18 of barrel 11 and against plunger inner 50. Replaceable needle assembly 30 comprises needle 31 that comprises cannula 32 and needle body 33 mounted to retractable needle mount 34 and mounting member 40. Barrel 11 comprises plunger end 12 at which is located releasing member 13, locking pawls 17A, 17B and finger grips 14A, 14B. Barrel 11 also comprises mounting portion 105 comprising "male" screw thread 1051 at needle end 15 onto which can be mounted complementary "female" screw thread 41 of mounting member 40 of replaceable needle assembly 30. It will also be appreciated that this male-female orientation may be reversed. Barrel seal 42 is also mounted at needle end 15 of barrel 11 to provide a seal between mounting member 40 and barrel 11. Barrel 11 further comprises needle mount retainer 60 at needle end 15 and fluid space 19. Needle cover 95 is also shown, which is removed in use.

Figure 2:
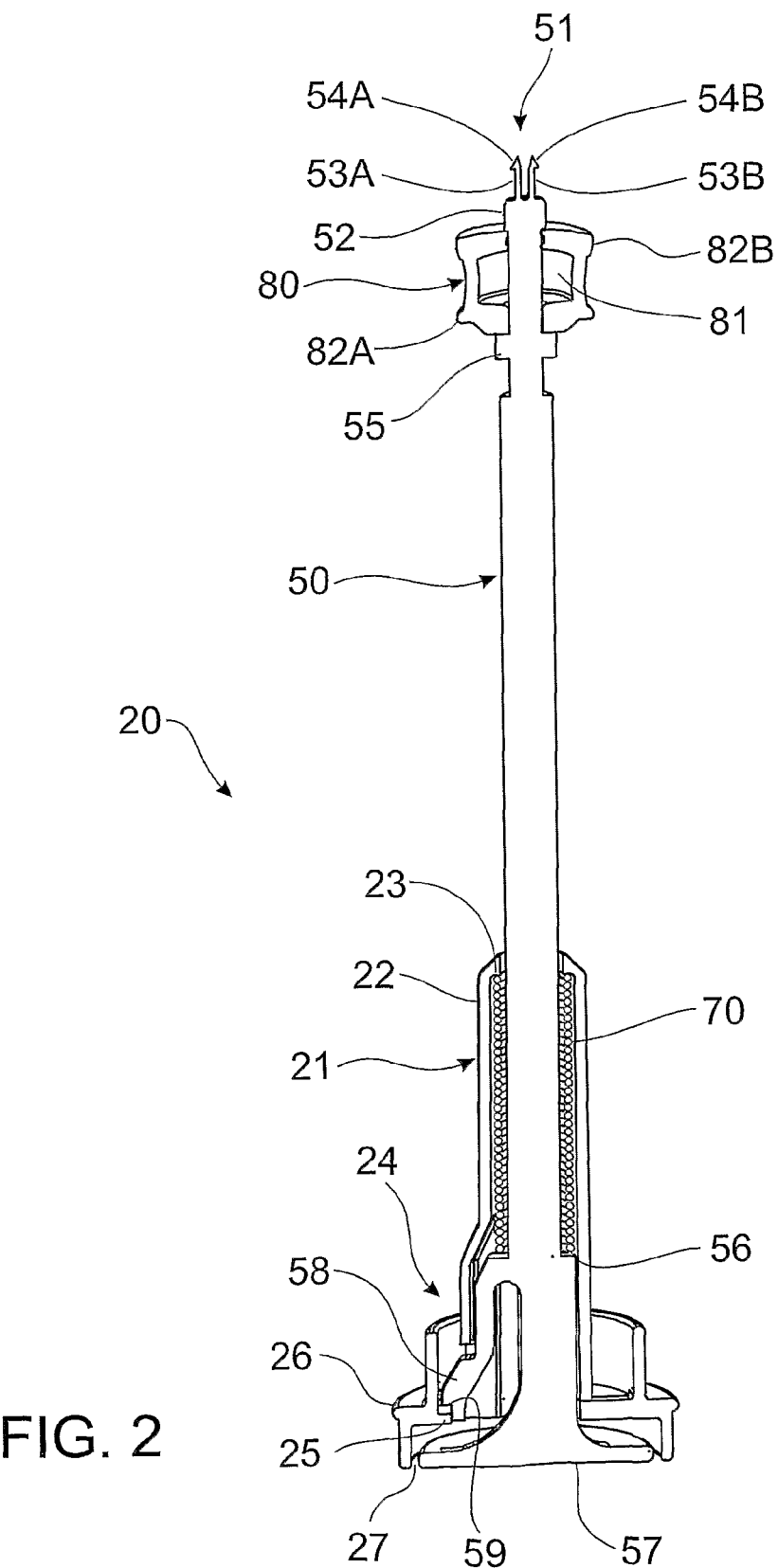
FIG. 2 is a sectional view of an embodiment of a plunger.

Referring now to FIG. 2, plunger 20 comprises plunger outer 21 comprising body 22, inner shoulder 23 and flange 24 having inner lip 25, rim 26 and button recess 27. Plunger inner 50 further comprises needle mount-engaging portion 51 that comprises needle mount release in the form of head 52 and arms 53A, 53B that respectively comprise barbs 54A, 54B. Plunger inner 50 further comprises abutment 55, inner ledge 56, button 57 operable by a user and trigger 58 comprising notch 59. Initially, notch 59 of trigger 58 engages inner lip 25 of plunger outer 21 to retain spring 70 in an initially compressed state, compressed between inner shoulder 23 of plunger outer 21 and inner ledge 56 of plunger inner 50. In this context, "initially compressed" means that spring 70 is compressed (i.e. energized) prior to use of retractable syringe 10.

Plunger seal 80 is mounted to plunger inner 50 and located between head 52 and abutment 55. Plunger seal 80 is collapsible or otherwise compressible or axially deformable by way of internally-located hollow chamber 81 and further comprises sealing ribs 82A, 82B which seals against inside wall 18 of barrel to prevent fluid leaking from fluid space 19.

Figure 3:
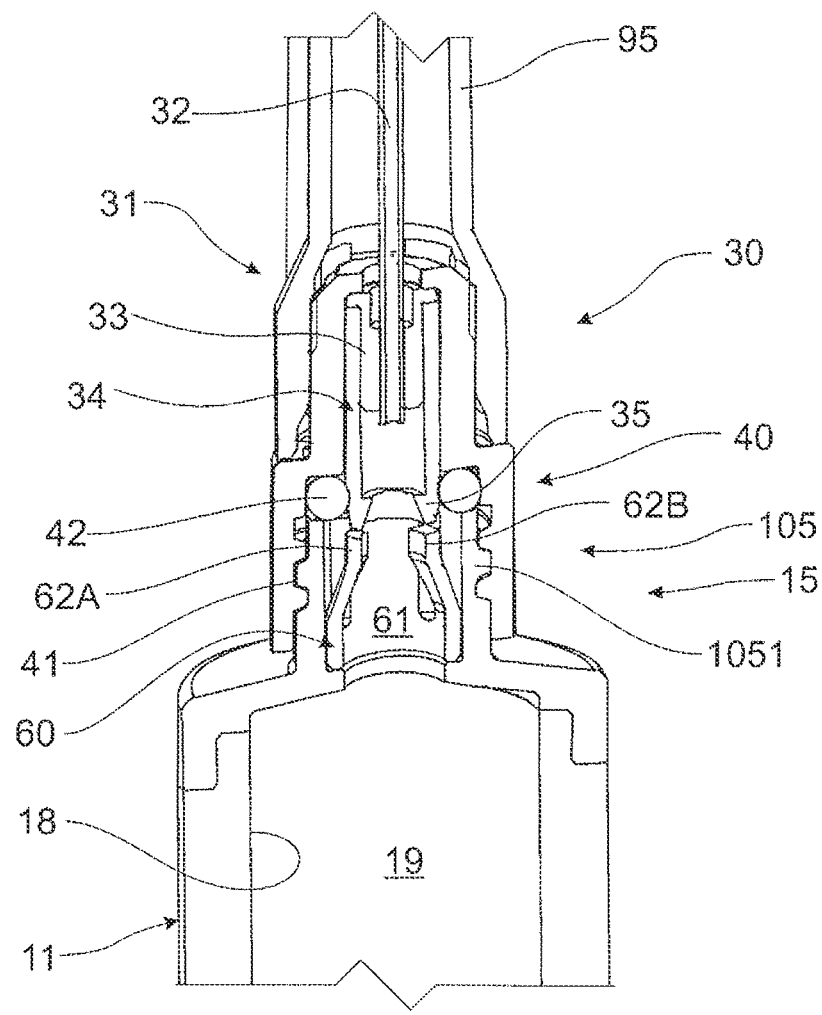
FIG. 3 is a sectional view of an embodiment of a replaceable needle assembly mounted on a barrel.

As shown in FIG. 3, replaceable needle assembly 30 comprises needle 31 that comprises cannula 32 and needle body 33 mounted to retractable needle mount 34 comprising annular base 35. Cannula 32 is glued to, or co-moulded with, needle body 33. Needle body 33 is glued to, interference fitted into, or co-moulded with, retractable needle mount 34. Needle mount retainer 60 comprises bore 61 and fingers 62A, 62B that bear against annular base 35 of needle mount 34 to prevent inadvertent axial movement of needle 31 and retractable needle mount 34 toward plunger end 12 of barrel 11. This could occur, for example, when a user applies a force to cannula 32 such as when piercing skin during injection.

Figure 4:
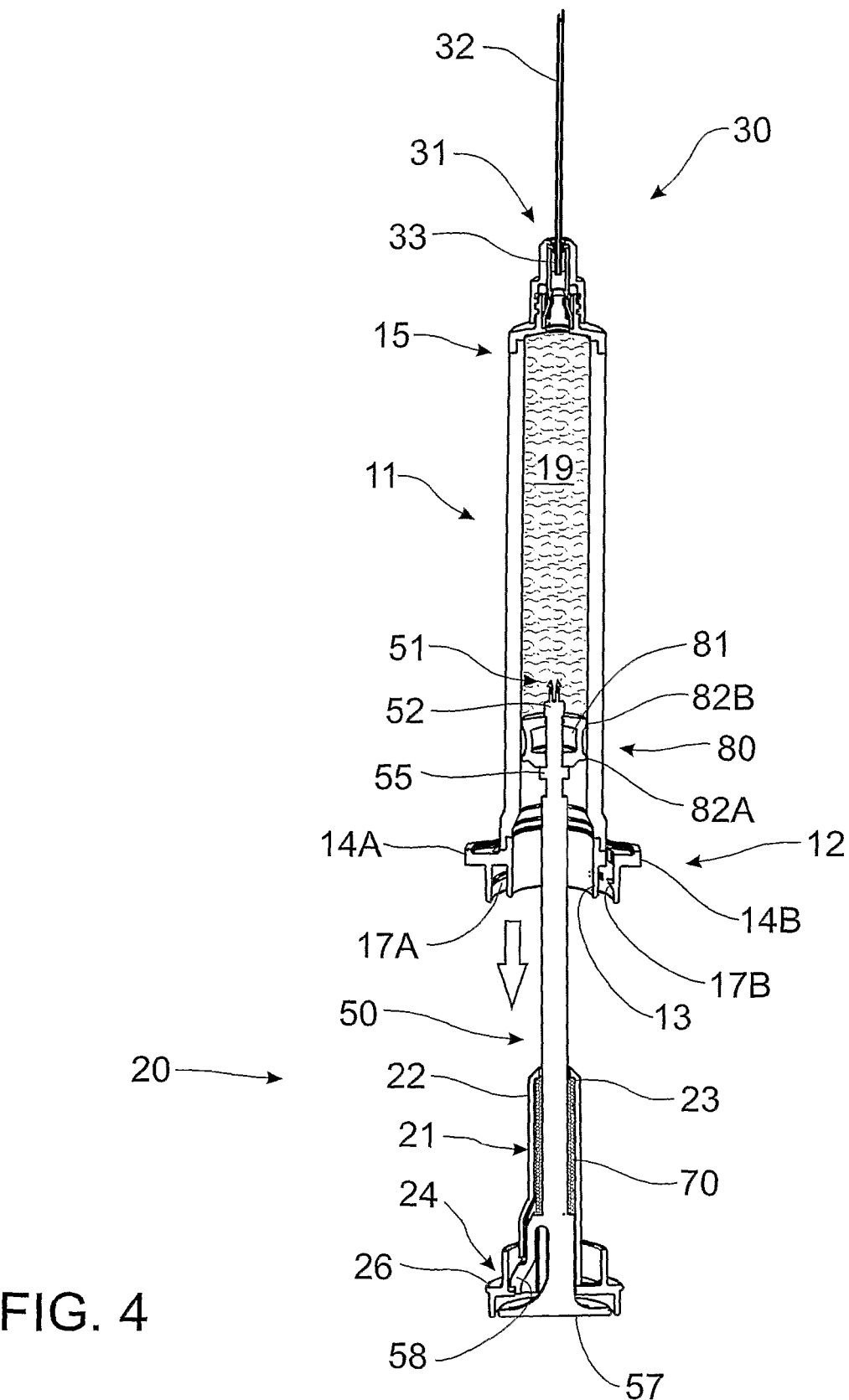
FIG. 4 is a sectional view of an embodiment of a retractable syringe during filling with fluid contents.

Referring now to FIG. 4, fluid space 19 of barrel 11 is filled with fluid contents by a user by moving plunger 20 axially away from needle end 15 of barrel 11. Optionally, particularly in the case of viscous fluid, the user may choose to fill barrel 11 using needle 31 having a larger cannula 32 and then replace needle 31 with a needle 31 having a smaller cannula 32 for injection. As is evident in FIGS. 5A and 5B, replaceable needle assembly 30 may be unscrewed from barrel 11 and another needle assembly 30 (e.g. with a needle 31 having a smaller cannula 32 or to replace a bent or burred cannula 32) screwed onto barrel 11, as indicated by the curved arrow in FIG. 5A.

Figure 6:
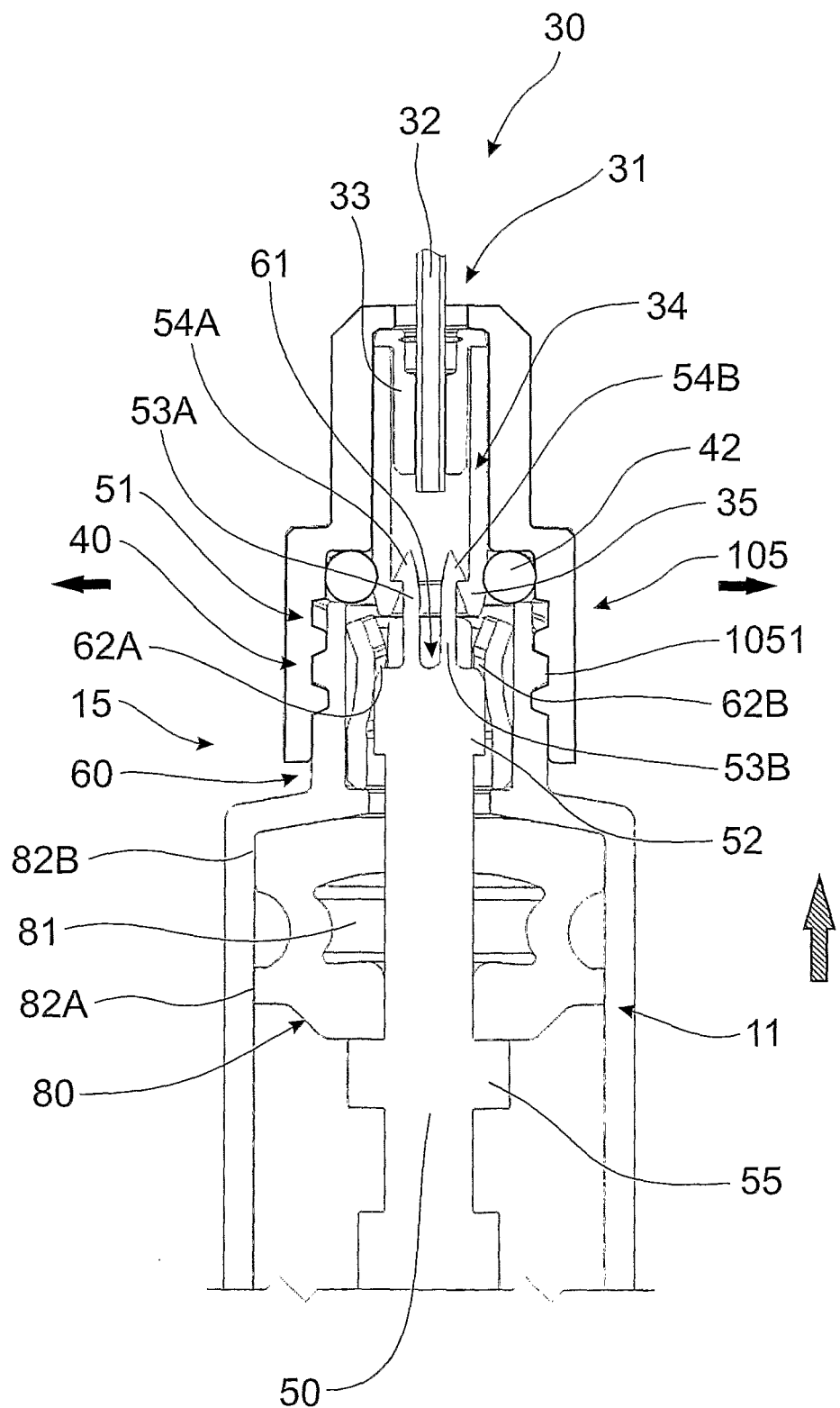
FIG. 6 is a sectional view of a plunger inner engaging a needle mount prior to needle retraction.

Referring to FIG. 6, to deliver fluid contents of syringe 10, plunger 20 is moved axially by the user in the direction of the hatched arrow toward needle end 15 of barrel 11. Towards the end of plunger 20 depression, collapsible seal 80 "bottoms out", but continued movement of plunger 20 in the direction of the hatched arrow in FIG. 6 is allowed by compression of seal 80. This continued axial movement of plunger 20 and collapsible seal 80 facilitates "squeezing out" remaining fluid to thereby assist delivery of the last remaining fluid contents of syringe 10. As evident in FIG. 6, this continued axial movement of plunger 20 allows arms 53A, 53B of needle mount engaging portion 51 to enter bore 61 in needle retainer 60, followed by head 52, until barbs 54A, 54B engage base rim 35 of needle mount 34. Head 52 acts to move fingers 62A, 62B of needle mount retainer 60 radially outwardly in the direction of the solid arrows in FIG. 6 out of contact with annular base 35 of retractable needle mount 34, thereby forming an unobstructed passageway in bore 61 of retainer 60, through which retractable needle mount 34 can be retracted.

Figure 7:
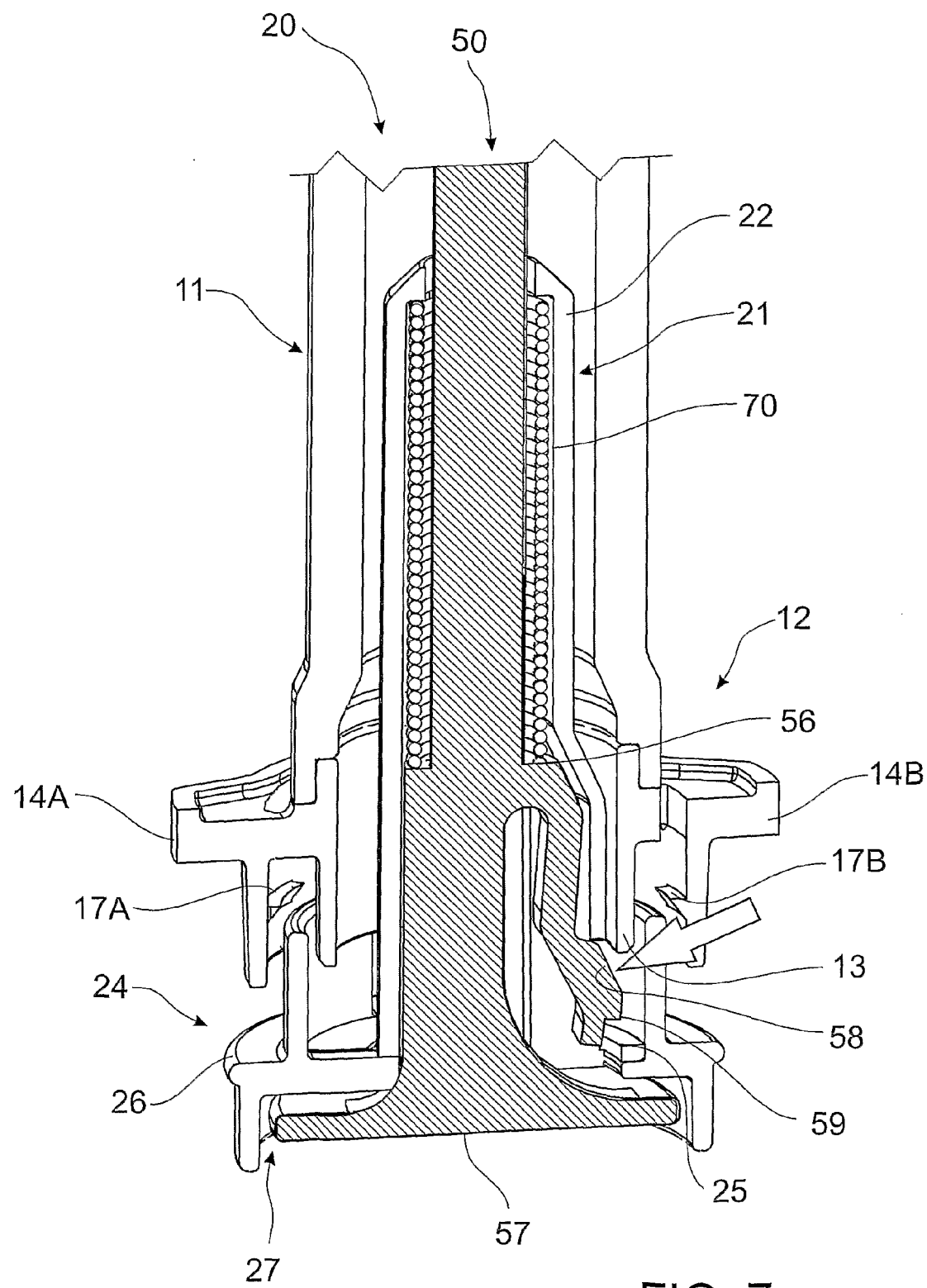
FIG. 7 is shows an embodiment of a retractable syringe lock formed between plunger outer and barrel and release of plunger inner from plunger outer.
Figure 8A:
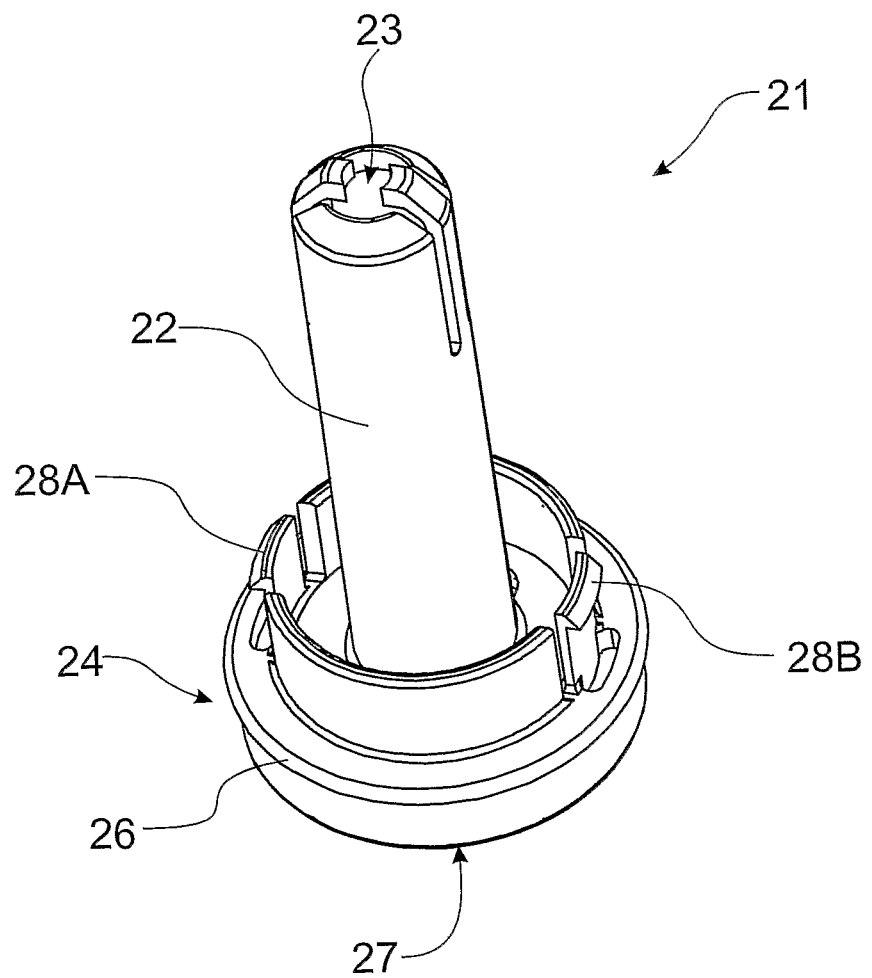
FIG. 8A is a perspective view of a plunger outer comprising hooked teeth and FIG. 8B is a sectional view of an embodiment of a retractable syringe during needle retraction.
Figure 8B:
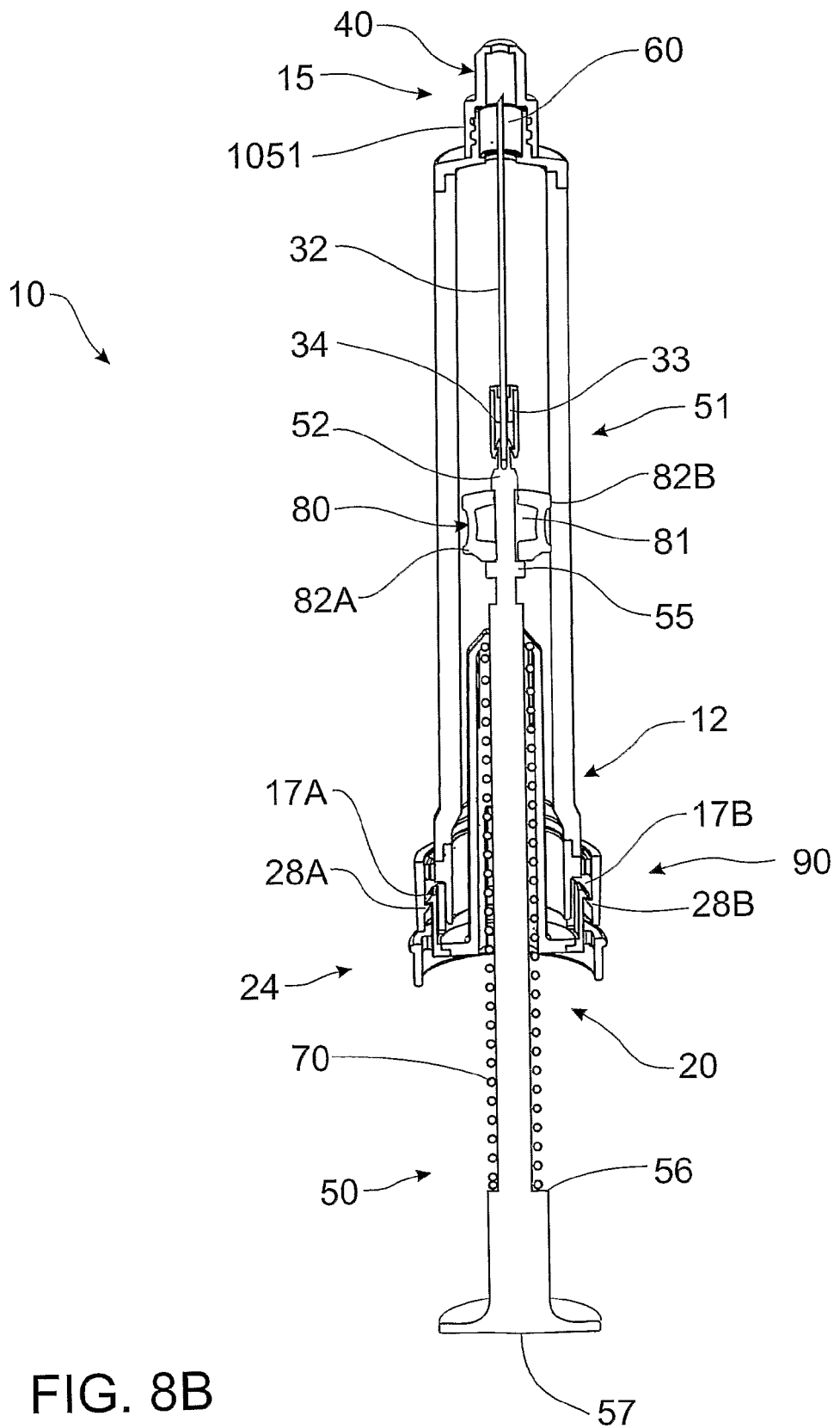

Reference is now made to FIG. 7, FIG. 8A and FIG. 8B. At the end of plunger 20 depression to deliver fluid contents of syringe 10 when needle mount engaging portion 51 of plunger inner 50 and needle mount 34 are coupled, a releasing member in the form of release ring 13 bears against trigger 58 of plunger inner 50, thereby moving trigger 58 radially inwardly in the direction of the solid arrow in FIG. 7. This disengages notch 59 from inner lip 25 of plunger outer 21, which thereby triggers release of plunger inner 50 from plunger outer 21 and allowing compressed spring 70 to decompress and forcibly bear against inner ledge 56 of plunger inner 50 to thereby retract plunger inner 50 and needle mount 34 coupled to needle mount engaging portion 51 of plunger inner 50. As best seen in FIG. 8A, plunger outer 21 comprises one or more locking elements in the form of hooked teeth 28A, 28B in underside of flange 24. As best seen in FIG. 8B, at the end of plunger 20 depression and before plunger inner 50 retraction, hooked teeth 28A, 28B of plunger outer 21 form lock 90 with one or more locking elements 17 of barrel 11, in the form of locking pawls 17A, 17B located at plunger end 12 of barrel 11, to thereby prevent withdrawal of plunger outer 21 from barrel 11. This also effectively prevents removal of plunger inner 50. In this regard, axial travel of retracting plunger inner 50 is limited by seal 80 bearing against locked plunger outer 21, so that plunger inner 50 and decompressed spring 70 cannot be removed from barrel 11.

As also shown in FIG. 8B, following retraction of plunger inner 50, needle mount 34, needle body 33 and cannula 32 are retracted into barrel 11 while retainer 60, mounting member 40 and barrel seal 42 remain at needle end 15 of barrel 11.

It will be appreciated from the foregoing that syringe 10 is arranged so that disengagement of plunger inner 50 from plunger outer 21 to allow decompression of spring 70 occurs only when fluid contents have been delivered and after needle mount engaging means 51 and needle mount 34 are coupled. This prevents inadvertent triggering of the retraction mechanism and ensures that needle mount 34 and needle 31 mounted thereto are retracted when the retraction mechanism is triggered.

The embodiment described in FIGS. 1-8 is particularly suited to a 3 mL or 5 mL capacity syringe 10.

Figure 9:
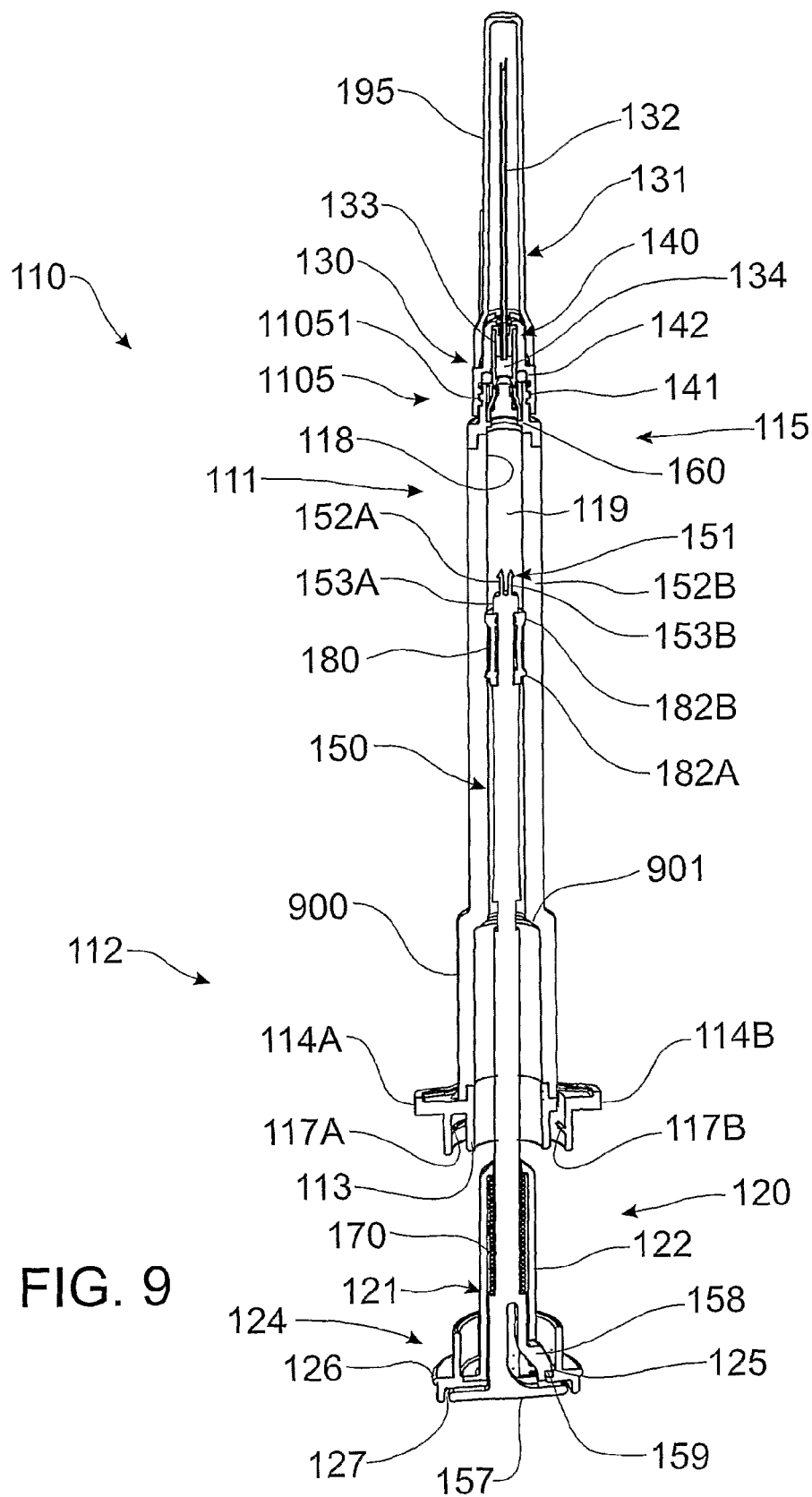
FIG. 9 is a sectional view of another embodiment of a retractable syringe.
Figure 10:
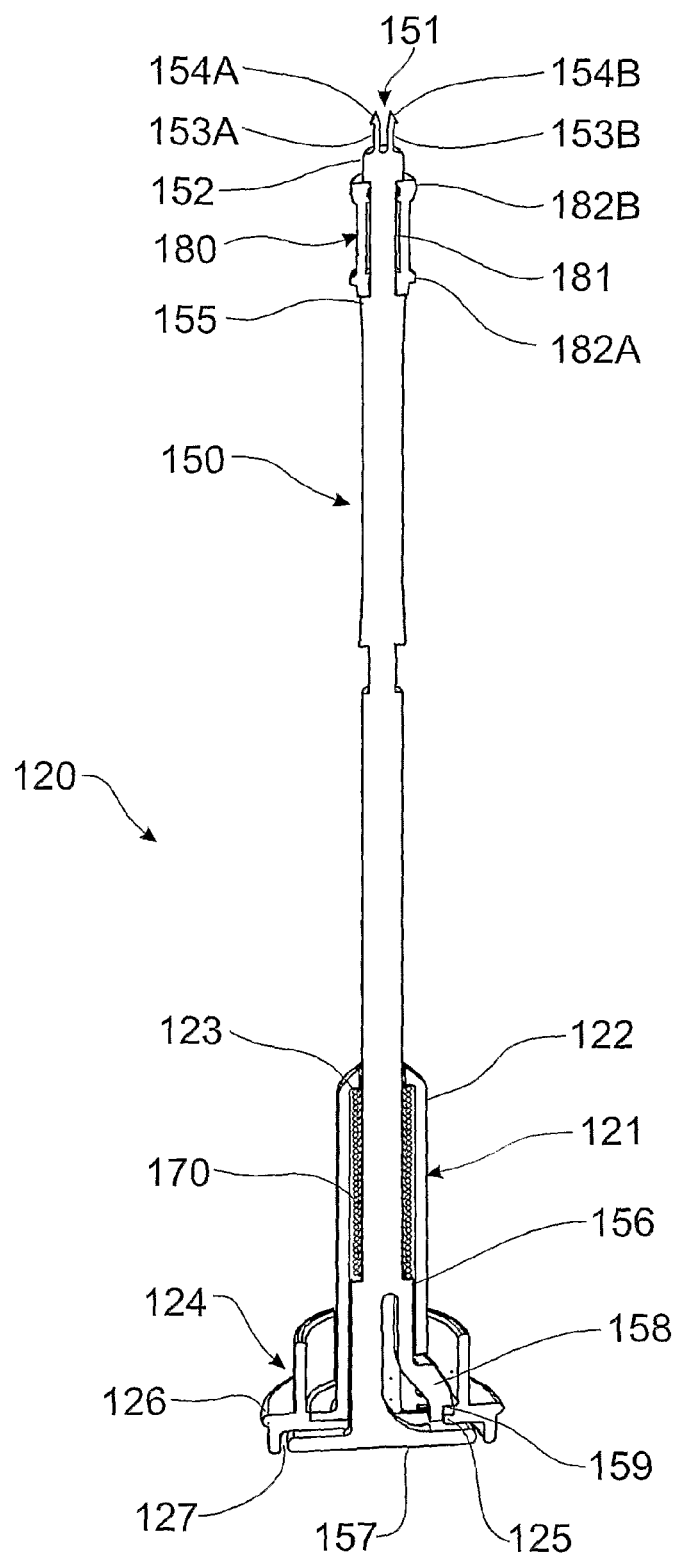
FIG. 10 is a sectional view of another embodiment of a plunger.

Reference is now made to FIGS. 9 and 10 which describe a related embodiment particularly suited to a 1 mL capacity syringe 110 comprising barrel 111 and plunger 120 having plunger inner 150 and plunger outer 121. Plunger seal 180 is mounted to plunger inner 150. Replaceable needle assembly 130 comprises needle 131 that comprises cannula 132 and needle body 133 mounted to retractable needle mount 134 and mounting member 140. Barrel 111 comprises plunger end 112 which comprises flared portion 900 which accommodates body 122 of plunger outer 121 and comprises inner waist 901 that limits axial travel of plunger 120 when delivering fluid contents of syringe 110. Plunger end 112 of barrel further comprises releasing member 113, locking pawls 117A, 117B and finger grips 114A, 114B.

Barrel 111 also comprises mounting portion 1105 comprising "male" screw thread 11051 at needle end 115 onto which can be mounted complementary "female" screw thread 141 of mounting member 140. Seal 142 is also mounted at needle end 115 of barrel 111 to provide a fluid-tight seal between mounting member 140 and barrel 111. Barrel further comprises needle mount retainer 160 at needle end 115. Needle cover 195 is also shown, which is removed in use.

Referring particularly to FIG. 10, plunger 120 comprises plunger outer 121 comprising body 122, inner shoulder 123 and flange 124 having inner lip 125, rim 126 and button recess 127. Plunger inner 150 further comprises needle mount engaging portion 151 that comprises head 152 and arms 153A, 153B that respectively comprise barbs 154A, 154B. Plunger inner 150 further comprises abutment 155, inner ledge 156, button 157 operable by a user and trigger 158 comprising notch 159. Initially, notch 159 of trigger 158 engages inner lip 125 of plunger outer 121 to retain spring 170 in an initially compressed state, compressed between inner shoulder 123 of plunger outer 121 and inner ledge 156 of plunger inner 150.

Plunger seal 180 is mounted to plunger inner 150 and is located between head 152 and abutment 155. Plunger seal 180 is collapsible or otherwise compressible or axially deformable by way of internally-located hollow chamber 181 and further comprises sealing ribs 182A, 182B which seal against inside wall 118 of barrel to prevent fluid leaking from fluid space 119 of barrel 111. Seal 180 shown in FIGS. 9 and 10 is relatively elongate in structure compared to seal 80 shown in FIGS. 1-8 given the relatively narrower internal diameter of barrel 111 of 1 mL syringe.

Needle mount 134 engagement and retraction by plunger inner 150 is essentially as described for the syringe 10 embodiment described in FIGS. 1-8. Similarly, lockdown of plunger outer 121 onto barrel 111 is also as described in FIGS. 1-8. Although not shown in FIG. 9 or 10, hooked teeth 128A, 128B of plunger outer 121 form lock 190 with locking pawls 117A, 117B located at plunger end 112 of barrel 111, to thereby prevent withdrawal of plunger outer 121 from barrel 111.

In light of the foregoing it will be appreciated that the present invention provides a relatively simple, robust and inexpensive syringe that is automatically disabled with little or no assistance from the user to thereby prevent, or at least minimize the likelihood of, re-use of the syringe or needle-stick injury to the user.

Furthermore, the replaceable needle assembly allows a user to select a needle of appropriate size of gauge or needle length and/or to replace a needle that becomes bent or burred. Another advantage of the retractable syringe described herein is that it can accommodate and fully encapsulate on retraction, needles of varying length up to 1.5 inches (~3.8 cm) in length, thereby providing great flexibility to the user.

It will also be appreciated that the collapsible plunger seal improves the efficiency of fluid delivery from the retractable syringe.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

The invention claimed is:

1. A retractable syringe subassembly for a retractable syringe including a plunger, the subassembly comprising:
   a barrel including a mounting portion having a male member,
   a replaceable needle assembly including
      a mounting member removably mountable to the barrel, said mounting member comprising a female member which is adapted to receive the male member of the mounting portion of the barrel,
      a retractable needle mount removably mounted to the mounting member and engageable by said plunger to facilitate retraction of the retractable needle mount, and
      a needle mounted to the retractable needle mount, and
   a needle mount retainer directly engaging the retractable needle mount to inhibit premature retraction of the retractable needle mount, the needle mount retainer being located in, and separately formed from, the barrel and which is configured to remain located in the barrel during replacement of the replaceable needle assembly.

2. The retractable syringe subassembly of claim 1, wherein the female member comprises a screw thread, and the male member comprises a screw thread complementary to the screw thread of the female member.

3. The retractable syringe subassembly of claim 2, wherein the needle mount retainer comprises fingers that retain said needle mount until retraction.

4. The retractable syringe subassembly of claim 3, wherein said fingers are movable radially outwardly to disengage from and release said needle mount for subsequent retraction.

5. The retractable syringe subassembly of claim 1, wherein the barrel further comprises a seal in use located between the mounting member and an inside wall of the barrel.

6. The retractable syringe subassembly of claim 1, wherein the barrel further comprises a releasing member.

7. The retractable syringe subassembly of claim 1, wherein the barrel further comprises one or more locking elements to form a lock with the plunger after retraction.

8. A retractable syringe kit comprising the retractable syringe subassembly of claim 1; a plurality of replaceable needle assemblies each including a mounting member removably mountable to the barrel, said mounting member comprising a female member which is adapted to receive the male member of the mounting portion of the barrel, a retractable needle mount removably mounted to the mounting member and engageable by said plunger to facilitate retraction of the retractable needle mount, and a needle mounted to the retractable needle mount, in combination with a plunger.

9. The retractable syringe kit of claim 8, said plunger comprising: a biasing means; a plunger inner; a plunger outer; and a collapsible seal mounted to the plunger inner; wherein the plunger inner and plunger outer co-operate to maintain said biasing means in an initially energized state prior to retraction.

10. The retractable syringe kit of claim 9, wherein the collapsible seal comprises an internal hollow chamber.

11. The retractable syringe kit of claim 10, wherein the collapsible seal allows axial movement of the plunger after delivery of fluid contents of the retractable syringe.

12. The retractable syringe kit of claim 9, wherein said plunger inner comprises a portion for engaging a retractable needle mount of a replaceable needle assembly.

13. The retractable syringe kit of claim 12, wherein, said portion for engaging the retractable needle mount comprises one or more barbed arms.

14. The retractable syringe kit of claim 9, which further comprises a needle mount release that facilitates disengagement of the needle mount from a needle mount retainer.

15. The retractable syringe kit of claim 9, the plunger inner further comprising a trigger which initially engages said plunger outer to maintain said biasing means in an initially energized state prior to retraction.

16. The retractable syringe kit of claim 15, arranged so that disengagement of said trigger from said plunger outer facilitates release of energy from said biasing means which facilitates retraction of said needle mount when coupled to said plunger inner.

17. The retractable syringe kit of claim 9, wherein said biasing means is a spring.

18. The retractable syringe kit of claim 9, wherein the plunger outer comprises one or more locking elements that form a lock with the barrel to prevent or hinder removal of the plunger outer from the barrel after retraction.

19. A retractable syringe comprising the retractable syringe subassembly according to claim 1; and a plunger.

20. A method of operating a retractable syringe according to claim 19, said method including the step of removably mounting the replaceable needle assembly to the barrel of the retractable syringe after filling the barrel with fluid contents for subsequent delivery.

21. The method of claim 20, wherein the method includes the step of screw-threadedly mounting the replaceable needle assembly to the barrel.

22. The retractable syringe of claim 19, said plunger comprising: a biasing means; a plunger inner; a plunger outer; and a collapsible seal mounted to the plunger inner; wherein the plunger inner and plunger outer co-operate to maintain said biasing means in an initially energized state prior to retraction.

23. The retractable syringe of claim 22, wherein the collapsible seal comprises an internal hollow chamber.

24. The retractable syringe of claim 22, wherein the collapsible seal allows axial movement of the plunger after delivery of fluid contents of the retractable syringe.

25. The retractable syringe of claim 22, wherein said plunger inner comprises a portion for engaging a retractable needle mount of a replaceable needle assembly.

26. The retractable syringe of claim 25, wherein, said portion for engaging the retractable needle mount comprises one or more barbed arms.

27. The retractable syringe of claim 22, which plunger further comprises a needle mount release that facilitates disengagement of the needle mount from the needle mount retainer.

28. The retractable syringe of claim 22, the plunger inner further comprising a trigger which initially engages said plunger outer to maintain said biasing means in an initially energized state prior to retraction.

29. The retractable syringe of claim 28, arranged so that disengagement of said trigger from said plunger outer facilitates release of energy from said biasing means which facilitates retraction of said needle mount when coupled to said plunger inner.

30. The retractable syringe of claim 22, wherein said biasing means is a spring.

31. The retractable syringe of claim 22, wherein the plunger outer comprises one or more locking elements that form a lock with the barrel to prevent or hinder removal of the plunger outer from the barrel after retraction.

32. The retractable syringe subassembly of claim 1 wherein a portion of the needle mount retainer is movable out of engagement with the retractable needle mount to facilitate retraction of the retractable needle mount.

* * * * *